United States Patent
Schillig et al.

(10) Patent No.: US 6,461,861 B2
(45) Date of Patent: *Oct. 8, 2002

(54) MICROBIAL MEMBRANE REACTOR FOR USE IN FLOW SYSTEMS

(75) Inventors: Henning Schillig, Braunschweig (DE); Inga Schneider, Braunschweig (DE); Christine Standfuss, Braunschweig (DE); Sabrina Heim, Braunschweig (DE); Tatjana Arnold, Braunschweig (DE); Sean Crispian Keeping, Shortlands (GB); Dieter Binz, Ladenburg (DE); Albrecht Vogel, Stutensee (DE)

(73) Assignee: ABB Limited, Staffordshire (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/444,403

(22) Filed: Nov. 22, 1999

(65) Prior Publication Data

US 2002/0034818 A1 Mar. 21, 2002

Related U.S. Application Data

(63) Continuation of application No. PCT/GB98/01505, filed on May 22, 1998.

(30) Foreign Application Priority Data

May 23, 1997 (DE) .......................................... 197 21 477

(51) Int. Cl.$^7$ ................................................ C12M 1/34
(52) U.S. Cl. ................................ 435/287.1; 435/287.9; 435/297.2; 435/817
(58) Field of Search ........................... 435/288.5, 287.1, 435/287.9, 297.2, 817; 436/52, 62, 63; 204/403, 415; 422/79

(56) References Cited

U.S. PATENT DOCUMENTS

| 4,667,504 | A | * | 5/1987 | Nobson | 73/38 |
| 4,734,372 | A | * | 3/1988 | Rotman | 435/291 |
| 5,053,060 | A | * | 10/1991 | Kopf-Sill et al. | 55/16 |
| 5,160,604 | A | * | 11/1992 | Nakamura et al. | 210/85 |
| 5,190,878 | A | * | 3/1993 | Wilheim | 435/285 |
| 5,468,605 | A | * | 11/1995 | Harris et al. | 435/4 |
| 5,536,662 | A | * | 7/1996 | Humphries et al. | 435/287.1 |
| 5,599,688 | A | | 2/1997 | Grass | |

FOREIGN PATENT DOCUMENTS

| DE | 37 31 864 | 3/1989 |
| DE | 44 18 941 | 12/1995 |
| FR | 2 647 118 | 11/1990 |
| GB | 2 048 711 | 12/1980 |
| WO | WO 85/01962 | 3/1985 |
| WO | WO 96/40860 | 12/1996 |

* cited by examiner

*Primary Examiner*—William H. Beisner
(74) *Attorney, Agent, or Firm*—Larson & Taylor, PLC

(57) ABSTRACT

A microbial membrane reactor for use in flow systems comprises a first element to receive the microorganisms and a second element to receive the flow channels. The two elements have planar interior surfaces which are pressed together separated by a membrane impervious to the microorganisms. The flow channels arranged in or on the surface of the second element serve to transport the liquid along the membrane so that the liquid can interact with the microorganisms arranged on the other side of the membrane. The geometry of the flow pathway and thus the geometry of the flow channels can be easily altered, in respect of the length, width and height of the channel, and adapted to practical requirements.

15 Claims, 4 Drawing Sheets

MICROBIAL MEMBRANE REACTOR FOR USE IN FLOW SYSTEMS

CROSS REFERENCE TO RELATED APPLICATION

Figure 1:
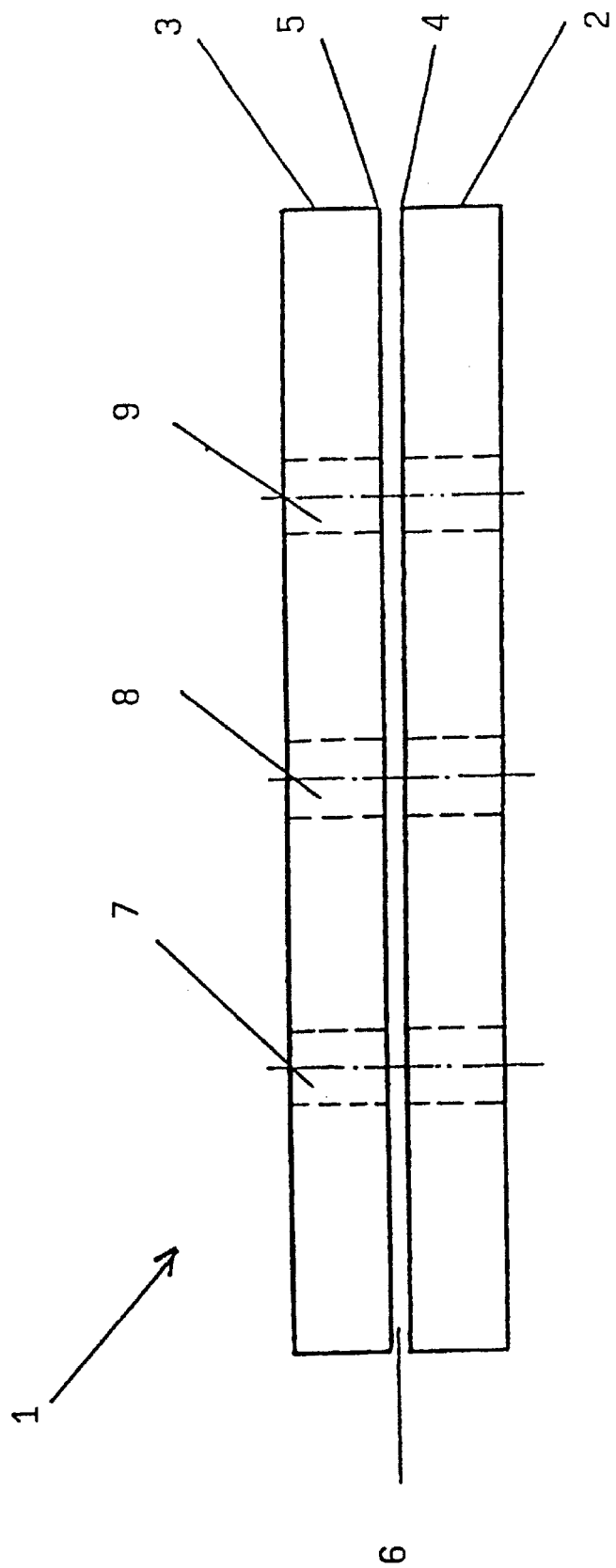

This application is a continuation of International Application No. PCT/GB98/01505 filed on May 22, 1998 (International Publication No. WO 98/53045).

This invention relates to a device for carrying out a procedure, for example an analytical procedure, in which microorganisms or other biological material interacts with components of a fluid.

Microorganisms are employed, because of their wide variety of metabolic pathways, for investigations into the biodegradability of various substances, for analytical purposes, for example for assaying individual substances or classes of substances, and for assessing the extent of pollution of water with biodegradable substances.

Frequently these procedures entail determining the metabolic activity of the microorganisms using suitable sensors. Thus the metabolic activity increases when the sample to be investigated contains substances which are used by the microorganisms as nutrients. Thus, biological oxygen demand (BOD), which is used as indicator for water pollution, is based on determination of oxygen consumption through the metabolic activity of microorganisms which are incubated with the sample to be investigated.

Microorganisms can also be used as toxicity indicators, because the metabolic activity decreases in the presence of toxic substances which lead to a reduction in the activity or even to death of the cells.

Microorganisms can in the above applications be employed as conventional cultures in minireactors or shake cultures in order to follow the metabolic activity of the cells, for example on the basis of the oxygen consumption or the cell growth, over a lengthy period. However, for some years there have also been approaches to shortening the analysis times required by automating sample delivery and shortening the incubation time, especially when it is not necessary to achieve an equilibrium state. In addition, microorganisms can be combined directly with the detectors by enclosing the microbial cells in polymers directly on electrodes or between membranes. Also in some circumstances polymers may be used in which the organisms are embedded for additional protection. These membranes may be fixed adjacent to a detector, for example an electrode with special mounting devices.

Microbial sensors, for example for determining a BOD value, may be fabricated in this way. However, if these sensors are used as detectors in automated analytical systems, special forms of construction need to be provided on the microbial membrane to enable the sample to be passed over the membrane. As a rule, only a small part of the membrane then comes into contact with the sample and for only a short time. The active surface of the membrane, which is restricted by the size of the detector and sample delivery construction, has a limiting effect, as a result of which only a restricted amount of microorganisms can be actively utilized.

Other forms of construction consist of cartridges (known from the use of immobilized enzymes) which are filled, as small columns, with polymers or glass particles on which enzymes or other proteins can be immobilized. Compared with membranes, they have the advantage that the amount of proteins which can be actively utilized is limited only by the size of the cartridge. In addition, because the sample flows through the cartridges of this type, a good contact between proteins and sample is ensured, and thus a good conversion of the analyte is achieved, which leads to relatively large signals. Cartridges of this type are used in flow systems in which the detector is then located downstream.

It is possible in principle to enclose microorganisms in cartridges of this type, because microorganisms can be adsorbed onto porous carriers. However, flow through the reactors is successful only when the internal pressure in the cartridge is not too high. The internal pressure depends, on the one hand, on the particles used to adsorb the cells and, on the other hand, on the mesh width of the gratings used to retain the particles in the cartridge. The fact that the cells are merely adsorbed onto the carrier particles means that they can also be washed off. If the mesh width of the gratings is so small that not only the particles but also washed-off microorganisms are retained in the cartridge, then the internal pressure becomes so high that conventional peristaltic pumps and, even more so, micropumps can no longer ensure transport of the sample through the cartridges. However, without appropriate membranes the microorganisms are discharged from the system, which can lead to falsification of the signals. An additional factor is that in cartridges of this type, reproducible cell loading can be achieved only with difficulty because the number of cells adsorbed on carriers cannot be easily regulated.

The invention is therefore based on the object of developing a novel device for contacting microorganisms or other biological material with fluids, e.g. liquids to be analyzed. The invention particularly relates to microbial membrane reactors for use in a flow system, in which microorganisms can be introduced easily and reproducibly, and discharge of the organisms from the reactor is prevented.

It will be appreciated that where in the following description, microorganisms are referred to, other biological materials may be employed instead of microorganism as such. Thus the term "microorganism" is intended to embrace not only prokaryotic and eukaryotic unicellular organisms but also cells or tissues of human, plant or animal origin.

Thus where the term "microbial membrane reactor" is used, it is intended to refer to a device including a membrane provided with any of the forms of "microorganism" encompassed by the above definition.

According to the present invention there is provided a device for carrying out a process in which microorganisms or other biological materials interact with components of a fluid, comprising a membrane sandwiched between opposed surfaces of first and second structural elements, characterised in that the microorganisms or other biological materials are located between the first structural element and the membrane and the inner surface of the second structural element that abuts the membrane is provided with one or more flow channels for flow of said fluid over the surface of the membrane. The membrane, which is preferably sterile, may be permeable to the fluid and substances dissolved in the fluid, e.g. dissolved gases and substances that may be metabolised by or otherwise interact with the microorganisms.

The present invention paarticularly relates to a microbial membrane reactor for use in flow systems, which has a first element with a planar inner surface to receive the microorganisms and a second element which is likewise provided with a planar inner surface and on which at least one flow pathway is formed, where the first and second element are arranged with their insides in contact, and a sterile membrane is arranged between the elements.

The pore size of the sterile membrane is preferably chosen so that it is impervious to the microorganisms used. The microorganisms are preferably arranged in a microbial membrane located between the inner surface of the first element and the sterile membrane. In other words, the sterile membrane covers the microbial membrane in relation to the flow pathways.

The invention also includes reactors which do not use microbial membrane. This may be by, for example, directly applying the microorganisms to the side of the sterile membrane facing the first element. This might be achieved by filtering the cells through the sterile membrane. It is also possible furthermore for the microorganisms to be applied directly to the planar inside of the first element, for example by applying a solution, a gel or a paste etc., comprising the microorganisms.

The elements of the membrane reactor can preferably be connected together by fixing means, for example by screws which grip through appropriate passages bored in the elements so that the elements are pressed together. However, other connection techniques such as gluing or bonding are possible.

The flow pathways are preferably designed as flow channels, it being possible to alter the contact area between the flow channel and the microorganisms present in the microbial membrane through the dimensions of the flow channel and its geometry.

In addition, connecting bores at the start and end of each flow channel lead to the upper side of the second element in order to be able to connect the liquid flow to the flow channel and thus define the flow pathway.

The flow channels are preferably formed in the inner surface of the substrate of the second element, for example by etching, cutting or another material-removing technique. However, the flow pathways can also be formed in a sheet which is applied to the planar inner surface of the second element, in which case the second element has corresponding connecting channels to connect the flow pathways of the sheet to the liquid flow. The flow channels can also be produced by material-adding processes on the planar inside of the second element, which then assumes the function of a substrate. A structural coating of this type would be, for example, the application of a paste by a screen printing technique with subsequent curing by drying or baking etc. Processes of these types are known to the skilled person from thick film technology and therefore do not need to be explained in detail here.

The microorganisms are preferably located on or in the microbial membrane which is placed on the inner surface of the first element. This may take the form of filter paper through which a cell suspension has been filtered. The number of cells adsorbed on the filter paper depends on the number of cells in the suspension. This can easily be assessed via the turbidity of the suspension, that is to say its optical density, and can thus also be more easily adjusted reproducibly than with the membrane or cartridge reactors of the prior art.

The microbial membrane may be covered in relation to the flow pathway or the flow channels with a membrane which has pores sufficiently fine for the microorganisms not to be discharged from the system, but so that nutrients and other substances which can be degraded are able to pass through. Since the liquid flow does not flow through the membranes but, because of the construction of the channels or of the sheet, only flows past them, these membranes do not lead to an increased buildup of pressure in the system.

It is thus possible with this type of reactor for the numbers of cells not only to be adjusted very reproducibly but also for the number of cells not to change due to discharge from the system. In contrast to cartridge reactors, the buildup of pressure through the reactor is very much less because no particles are present in the membrane reactor. This means that this type of reactor is also suitable for combining with micropumps with only low capacities. In addition, the contact area between the flow pathway and the microorganisms is very much larger and can easily be altered through the dimension of the flow channel, that is to say its diameter, length or the geometric shape. This means that effective utilization of the enclosed cells is possible, even if there is a system-related change in the limiting conditions. It is furthermore possible easily to manufacture multichannel reactors which are advantageous for ensuring longer operating times and for shortening the time between successive analysis steps. This is because the cells after having been incubated with a sample need to recover from this pollution and to be subjected to rinsing steps. These rinsing steps frequently limit the frequency with which successive analysis procedures can be carried out. It is possible on use of a multichannel system for the incubation with the sample to take place in one channel, while the regeneration of the cells takes place in another channel.

The devices provided according to the invention therefore have the following advantages over the prior art:

- the microorganisms may be located on a membrane which is covered with a membrane acting as sterile barrier. This prevents discharge of cells from the reactor.
- the microorganisms can be applied to the "microbial" membrane by filtration of a cell suspension, which makes it possible easily to vary the cell loading and, at the same time, makes good reproducibility of cell loading possible.
- the reactor contains no particles to which microorganisms are applied, so that no additional internal pressure is built up.
- it is possible by varying the geometry of the flow pathway for the contact time between the sample and the cells to be varied and adapted to practical requirements.
- the reactor can be manufactured in various ways so that, for example, combinations with microsystems are easily possible.
- compact integration of a plurality of channels is possible.

It is furthermore possible to arrange necessary sensors downstream from the reactor, or they are placed in front of and behind the reactor for differential measurement. Examples of suitable sensors are oxygen electrodes, but other sensors can also be employed depending on the analyte to be determined and microorganisms used, such as pH, $CO_2$, $NH_3$ or $Cl^-$ electrodes. The selection of the detectors depends on the particular requirements of the analysis procedures being carried out.

Figure 2A:
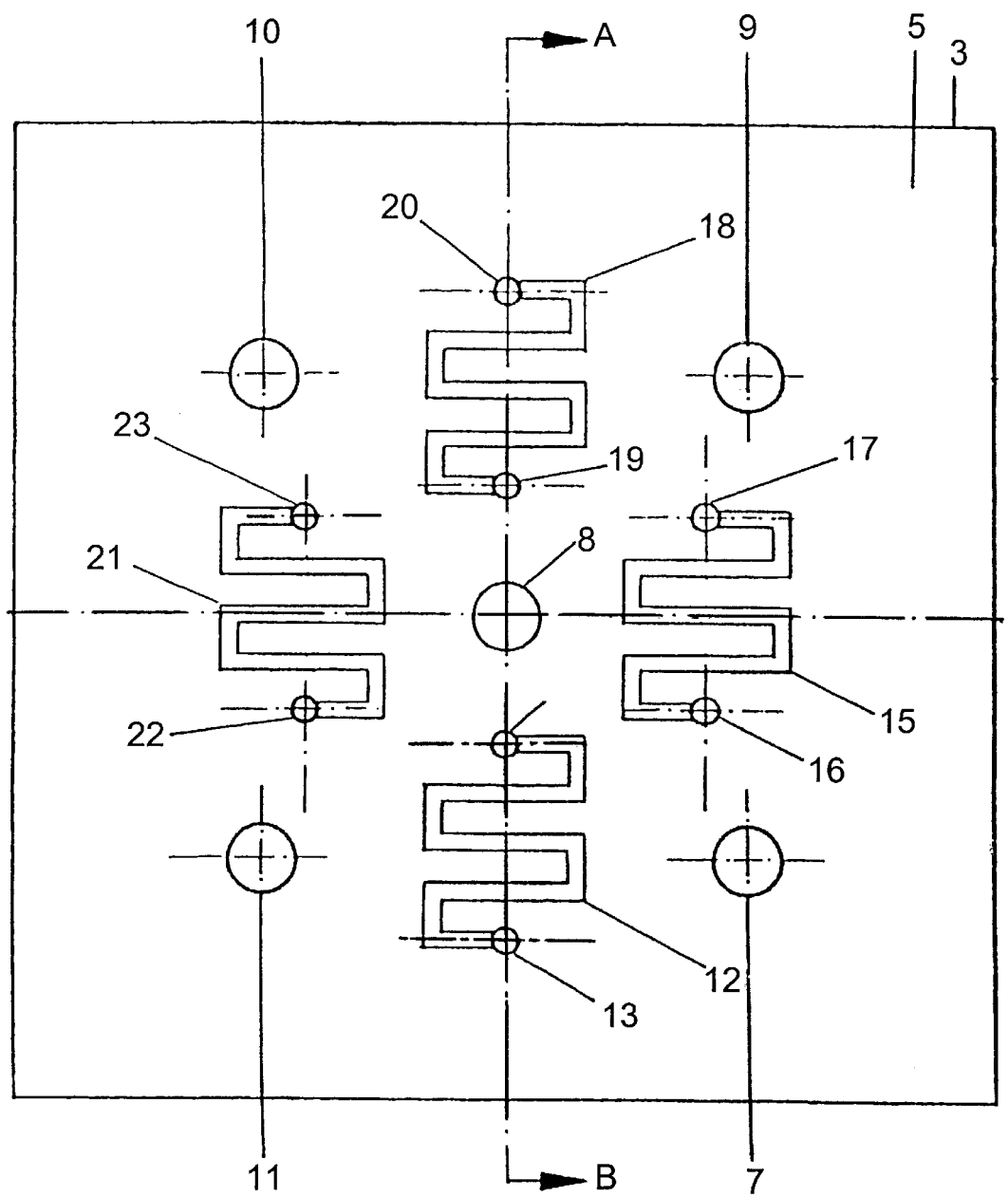
Figure 2B:
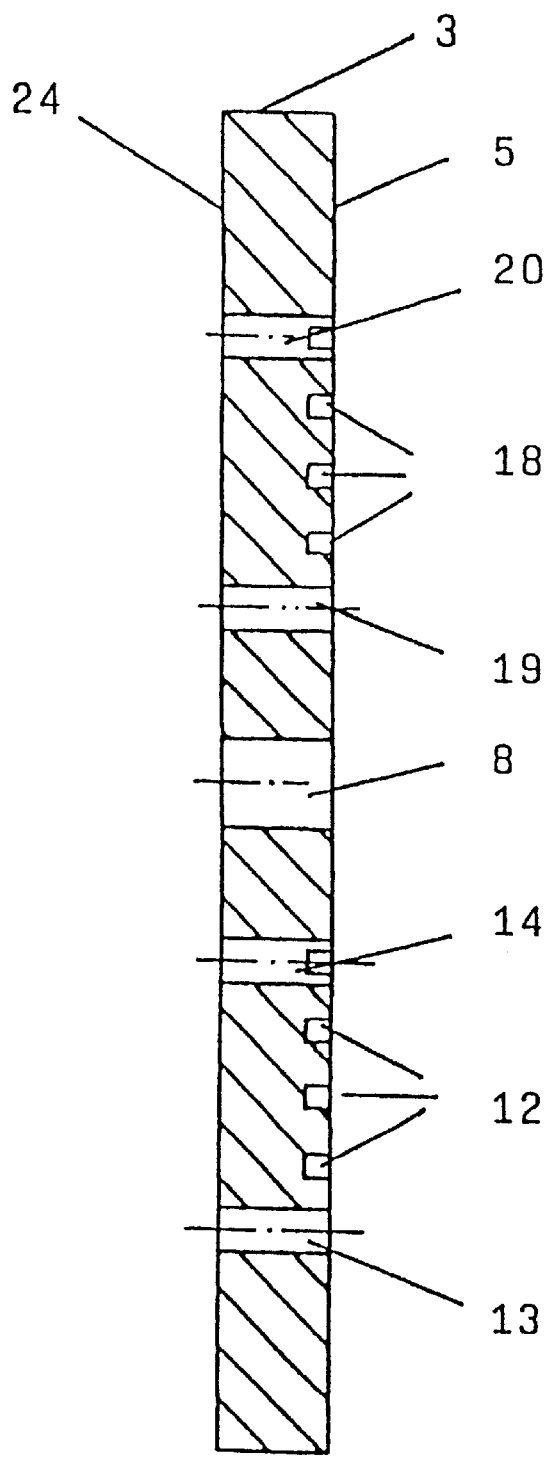
Figure 3:
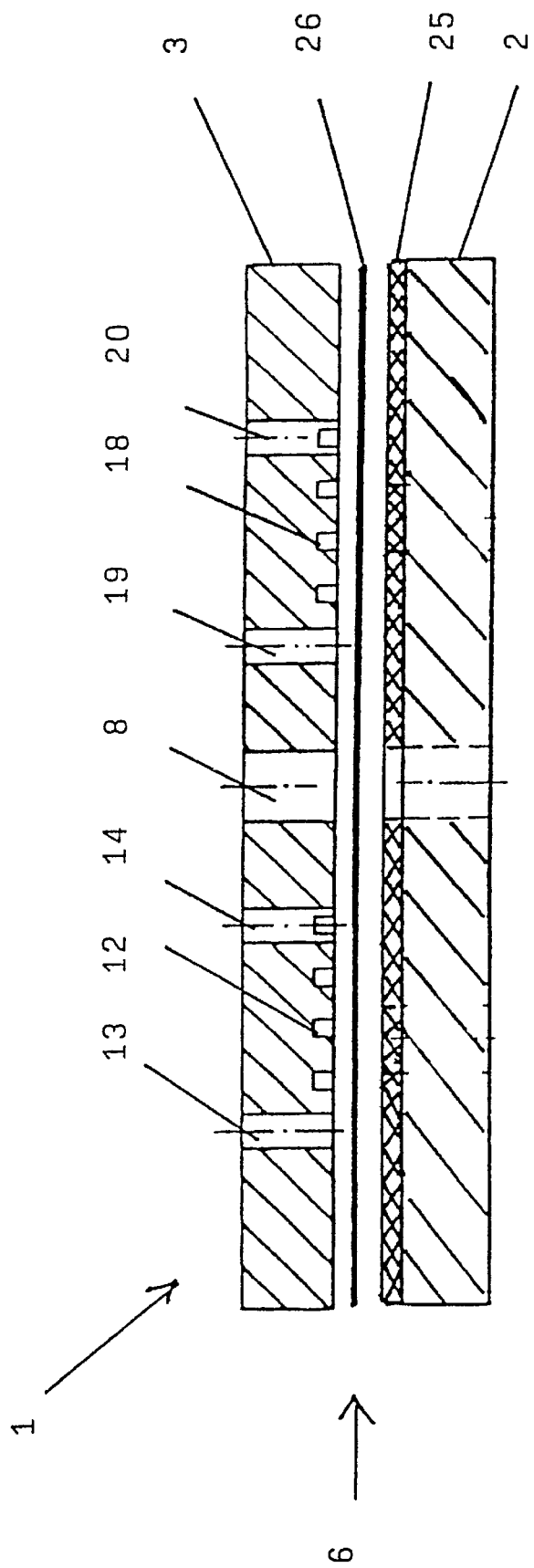

The invention will now be described by way of example with reference to the accompanying drawings, in which FIG. 1 shows a cross-section through a microbial membrane reactor according to the invention, FIG. 2a shows a top view of the inside of the second element of the microbial membrane reactor, FIG. 2b shows a cross-section through the second element of the microbial membrane reactor along the line A–B in FIG. 2a and FIG. 3 shows a diagrammatic representation of the cross-section of a microbial membrane reactor with membranes indicated diagrammatically.

Referring to the drawings, FIG. 1 shows in cross-section the diagrammatic arrangement of the microbial membrane reactor 1, consisting of a first, or in the drawing lower, part 2 which serves to receive a membrane (not depicted), and of a second corresponding upper element 3 which carries or contains the flow channels explained later. It is evident from the cross-section that the respective insides 4 and 5 of the corresponding lower and upper elements 2, 3 form a planar surface. In the gap 6 between these planar surfaces 4, 5 there are arranged a so-called sterile membrane (not depicted) and the microbial membrane.

The elements 2, 3 of the microbial membrane reactor 1 are pressed together, with the membranes arranged between them, by means, for example, of screws passing through bores 7, 8 and 9 which extend through the two elements 2 and 3. The flow channels can in this case either be arranged directly in the surface 5 of the element 3 in the form of depressions or troughs, or can be formed by grooves in a sheet which is introduced, in addition to the membranes, on the surface 5 of the element 3 in the gap 6 before assembly of the elements 2, 3. The membranes and the optional sheet or the flow channels are omitted in this figure for reasons of clarity.

FIG. 2a shows a top view of the inner surface 5 of the upper or second element 3 which contains the flow channels. To assemble the microbial membrane reactor 1, the second element 3, and the first element 2 which is not depicted here, contain bores 7, 8, 9, 10 and 11. The embodiment of the second element depicted here contains a multiplicity of channels 12, 15, 18 and 21, which are designed to meander, and where each channel is connected by corresponding bores 13, 14; 16, 17; 19, 20; 22, 23 to the upper side of the second element 3, which side is preferably likewise planar so that one element 2, 3 of the microbial membrane reactor 1 has, in the preferred embodiment, a square flat shape in the form of a block. However, this shape is not obligatory; on the contrary, only planar inner surfaces of the elements 2, 3 of the microbial membrane reactor 1 are a prerequisite.

The shape or the number of the flow channels 12, 15, 18, 21 depends on the particular requirements of the use to which the device is to be put. The internal volume of the flow channels 12, 15, 18, 21 (length, width, depth) can be chosen appropriately by suitable fabrication techniques. This can take place, for example, by using microfabrication techniques, in which case "flow micro-channels" are produced in wafers by suitable process control. The geometric shape of the channels themselves which is shown here does not necessarily have to be applied in the surface of the inside of the second element 3, but can be achieved by appropriate grooves in a separate sheet (not depicted) which is then placed on the inside 5 of the second element 3 in such a way that the channels 12, 15, 18, 21 of the sheet coincide with the corresponding bores 13, 14; 16, 17; 19, 20; 22, 23. In this case, the depth of the channels depends on the thickness of the sheet used. In a top view therefore a sheet would likewise correspond to the depiction in FIG. 2a.

FIG. 2b shows the second element 3 of the microbial membrane reactor 1 in the cross-section along the line A–B in FIG. 2a. The appropriate channels 12, 18 are excavated in the inside surface 5 of the first element 3, for example by etching or another material-removing technique. The connection points and end points of the channels are connected to the corresponding bored passages 13, 14, 19, 20 which lead to the upper side 24 of the second element. These bored passages serve as connection elements for connection of the external liquid flow.

FIG. 3 shows a cross-section through the microbial membrane reactor 1 with diagrammatically depicted membranes along the line A–B in FIG. 2a. A microbial membrane 25 which contains the microorganisms is applied to the first or lower element 1 of the reactor. The membrane 25 can be formed, for example, by a conventional filter paper. The sterile membrane 26 which is impervious to microorganisms is arranged above this microbial membrane 25 and keeps the microorganisms away from the flow channels 12, 18 of the second or upper element 3. The upper and lower element 2, 3 are pressed together by screws inserted along the depicted passage hole 8, so that the gap 6 depicted in FIG. 3 is, of course, absent from a reactor 1 ready for use.

What is claimed is:

1. An analysis device comprising a microbial membrane reactor for carrying out an analytical process in an analytical flow system in which microorganisms or other biological materials interact with components of a fluid, the reactor comprising a membrane sandwiched between opposed surfaces of first and second structural elements, characterized in that the microorganisms or other biological materials are located between the first structural element and the membrane and the inner surface of the second structural element that abuts the membrane is provided with one or more flow channels for flow of said fluid over the surface of the membrane.

2. A device according to claim 1, characterized in that said opposed surfaces are substantially planar.

3. A device according to claim 1 characterized in that the reactor has a first element with a planar inner surface to receive microorganisms, and a second element which is provided with a planar inner surface wherein at least one flow pathway is formed on said inner surface of the second element, where the first and second elements are arranged with their planar inner surfaces in contact, and a sterile membrane is arranged between the elements.

4. A device according to claim 3, characterized in that the pore size of the sterile membrane is selected so as to be impervious to the microorganisms used.

5. A device according to claim 1, characterized in that the microorganisms or other biological material are provided in the form of a membrane between the inner surface of the first element and the sterile membrane.

6. A device according to claim 1, characterized in that the first and the second elements are connected together by fixing means and are pressed together.

7. A device according to claim 6, characterized in that the fixing means are screws arranged in appropriate passages bored in the elements.

8. A device according to claim 6, characterized in that the elements are glued together or bonded to one another.

9. A device according to claim 1, characterized in that the contact area between the flow pathway designed as flow channel and the microorganisms present in the microbial membrane are determined by the dimensions of the flow channel and its geometry.

10. A device according to claim 9, characterized in that connecting bores at the start and end of each flow channel lead to the upper side of the second element so as to permit connections for liquid flow to be made to selected flow channels.

11. A device according to claim 1, characterized in that the flow channels are formed as recesses and/or grooves in the substrate of the second element in said inner surface.

12. A device according to claim 1, characterized in that the flow channels are formed in a separate sheet which is applied to said inner surface of the second element, and wherein the second element has corresponding connecting bores so as to provide connections for liquid flow to be made to the flow channels of the sheet.

13. A device according to claim 1, characterized in that the flow channels are produced by forming a structural coating on said inner surface of the second element.

14. A device according to claim 1, characterized in that the membrane is a semi-permeable membrane.

15. A device according to claim 1, characterized in that the membrane is permeable to the fluid or to substances dissolved in the fluid such as dissolved gases and substances that may be metabolised by or otherwise interact with the microorganisms.

\* \* \* \* \*